United States Patent
Muscarella et al.

(10) Patent No.: US 6,930,486 B2
(45) Date of Patent: Aug. 16, 2005

(54) CONDUCTIVITY SENSOR

(75) Inventors: Stephen B. Muscarella, Henrietta, NY (US); Philip T. Pascoe, Rochester, NY (US)

(73) Assignee: Pulsafeeder, Inc., Rochester, NY (US)

( * ) Notice: Subject to any disclaimer, the term of this patent is extended or adjusted under 35 U.S.C. 154(b) by 0 days.

(21) Appl. No.: 10/636,929

(22) Filed: Aug. 7, 2003

(65) Prior Publication Data

US 2004/0075439 A1 Apr. 22, 2004

Related U.S. Application Data

(60) Provisional application No. 60/419,566, filed on Oct. 18, 2002.

(51) Int. Cl.[7] .............................................. G01N 27/02
(52) U.S. Cl. ....................................... 324/446; 324/439
(58) Field of Search ................................ 324/439, 441, 324/444–450; 205/775, 193; 439/669

(56) References Cited

U.S. PATENT DOCUMENTS 4,147,596 A * 4/1979 Baboian et al. .......... 205/775.5
4,227,151 A * 10/1980 Ellis et al. .................. 324/448

* cited by examiner

Primary Examiner—Vincent Q. Nguyen
(74) Attorney, Agent, or Firm—Hodgson Russ LLP

(57) ABSTRACT

A conductivity probe having a modular design. A probe body has a distal end and a proximal end. The distal end includes a recessed portion for providing a seat for an O-ring that seals an electrode tip assembly. The probe body also includes a set of internal threads for engaging with cooperating threads disposed on the electrode tip assembly. The distal end of the body terminates in a bottom wall having an opening leading to a connection pipe attached to a junction box. The exterior of the probe body includes a stepped down profile of varying constant diameters with a side port formed in the probe body for receiving a temperature compensation probe. The probe body includes a set of external threads and wrench flats for installing the probe into a boiler conduit. The design is completely modular with minimal assembly required. The probe body is machined easily and features hard stops for trouble-free assembly. Also, there is no potting of the electrical components required.

27 Claims, 2 Drawing Sheets

CONDUCTIVITY SENSOR

CROSS-REFERENCE TO RELATED APPLICATION

This application claims the benefit of priority to U.S. patent application Ser. No. 60/419,566 filed Oct. 18, 2002.

FIELD OF INVENTION

The present invention relates to a conductivity probe suitable for use in environments where high temperature and high pressure conditions may be found. Conductivity measurements are also made in low temperature and low pressure environments. The features of this probe design are also useful in that kind of environment.

BACKGROUND OF THE INVENTION

Conductivity sensors are typically installed in boiler systems to provide a measurement of the dissolved solids in the system. By taking an electrical measurement of the conductivity of the fluids in the system, the life of the piping and equipment can be extended and the efficiency of the steam can be increased.

There is a need for a conductivity probe having a modular design that is easier to manufacture, easier to service and easier to upgrade than existing models.

SUMMARY OF THE INVENTION

The present invention meets the above-described need by providing a conductivity probe having a modular design. A probe body has a distal end and a proximal end. The distal end comprises a recessed portion for providing a seat for an O-ring that seals an electrode tip assembly. The probe body further comprises a set of internal threads for engaging with cooperating threads disposed on the electrode tip assembly. The distal end of the body terminates in a bottom wall having an opening leading to a connection pipe attached to a junction box.

The exterior of the probe body includes a stepped down profile of varying constant diameters to facilitate flow around the probe and rapid temperature response with a side port formed in the probe body for receiving a temperature compensation probe.

The probe body includes a set of external threads and wrench flats for installing the probe into a boiler sample line fitting.

The design is completely modular with minimal assembly required. The probe body is machined easily and features hard stops for trouble-free assembly and visual verification of sealing. Also, there is no potting of the electrical components as required by many competitive products.

BRIEF DESCRIPTION OF THE DRAWINGS

The invention is illustrated in the drawings in which like reference characters designate the same or similar parts throughout the figures of which.

DETAILED DESCRIPTION

Figure 1:
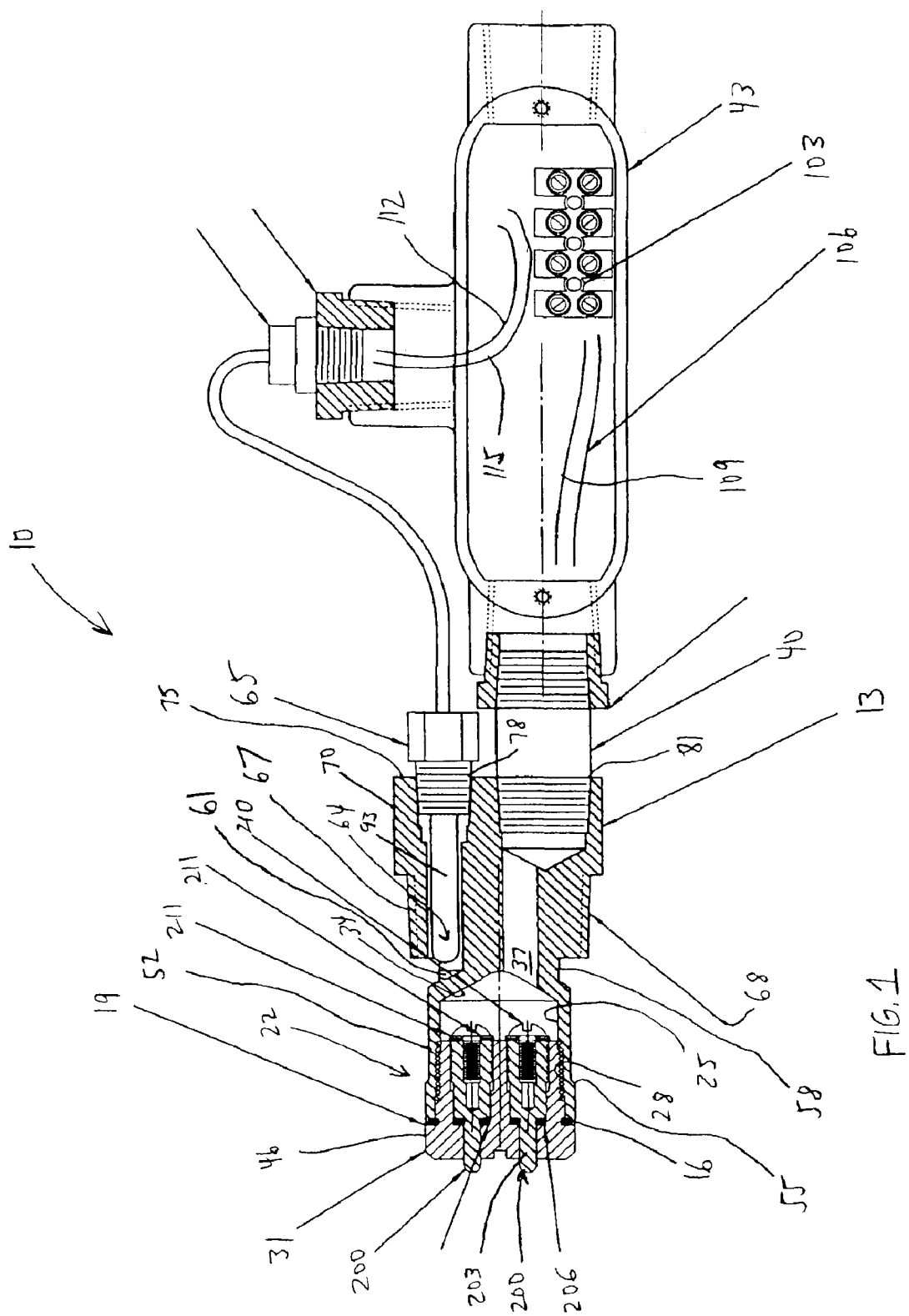
FIG. 1 is a sectional side view of the conductivity sensor of the present invention.

Referring to FIG. 1, a modular conductivity sensor 10 is shown. The modular design of the conductivity sensor 10 provides for individual components to be switched out for upgrades or repairs. The conductivity sensor 10 comprises a probe body 13. The probe body 13 may be constructed from any rigid material suitable for the environment where the sensor 10 is used. As an example, the body 13 may be formed out of stainless steel. The distal end of the body 13 may include a recessed portion 16 forming a seat for an O-ring 19. The body 13 has an outer wall 22 and an inner wall 25. The inner wall 25 may include a set of threads 28 for engaging with a removable electrode tip assembly 31. The inner wall 25 terminates at a bottom wall 34 having an opening 37 leading to a connection pipe 40 leading to a junction box 43. The outer wall 22 has a first section 46 having a constant diameter. The first section 46 is stepped down to a second section 52 having a smaller diameter. A transition 55 extends between the two sections. The second section 52 extends to a third section 58 having a smaller diameter and having an opening 61 that leads to a port 64 formed in the probe body 13 for receiving a temperature compensation probe 65.

The second section 52 and third section 58 are stepped down to provide suitable flow conditions inside the fitting where the sensor 10 is inserted so that the electrodes and temperature compensation probe function properly.

A fourth section 67 of the outer wall 22 provides for threaded engagement of the body 13 into a fitting. The standard installation is for 1 inch pipe (inside diameter) and the threads 68 are 1 inch NPT. The present invention can be modified to work in other sizes of conduits as well.

A fifth section 70 of the outer wall 22 is provided with wrench flats (not shown) for installation.

The fifth section 70 terminates at a bottom wall 75 having at least two openings 78 and 81.

Opening 78 provides a port for attaching the temperature compensation probe 65. The temperature compensation probe 65 may comprise a thermistor based system, RTD or other appropriate thermal measuring device. The probe 65 may have a metal or non-metal sheath 93 and is typically factory sealed. The probe 90 is available from several sources and may be attached to probe body 13 in many ways. In the example shown, the probe 65 includes NPT threads for engaging with threads in the probe body 13.

Opening 81 provides a port for a connection pipe 40 that attaches at a first end to the probe body 13 and attaches at an opposite end to the junction box 43. In the example shown, the connection pipe 40 is a separate member, but could be formed integrally in the probe body 13.

The junction box 43 includes a color-coded wire terminal block 103 for connecting electrode leads 106 and 109 and the leads 112, 115 from the temperature compensation probe 65.

The electrode tip assembly 31 is constructed of a suitable insulator material for supporting electrodes 200. The electrodes 200 may be formed as a pair of solid metal pin 203 disposed in spaced apart relation. The electrodes 200 are received in cylindrical bores disposed toward the center of the electrode tip assembly 31. The openings step down such that a ledge is formed around the opening. O-rings 206 are disposed in a face seal arrangement against the ledge to seal around the individual electrode pins 200. Screws 210 are provided for establishing a connection between the lead wires 109 and 106 and electrical terminals 211 for electrodes 200.

Figures 2A, 2B:
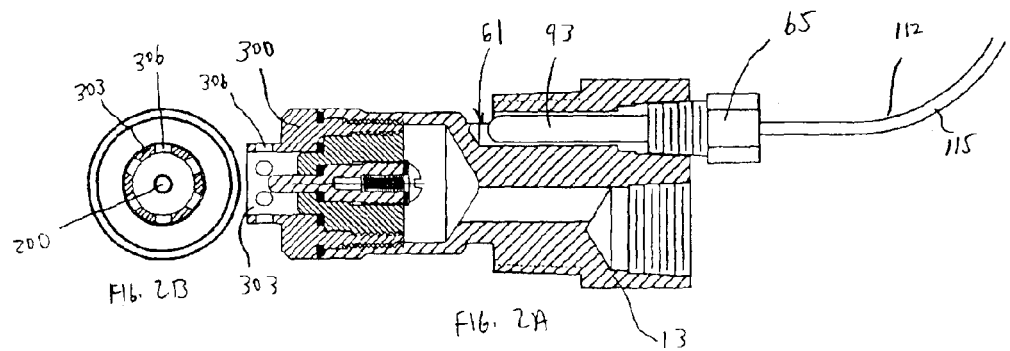
FIG. 2A is a sectional side view of an alternate electrode tip assembly that uses the body of the probe as an electrode to minimize installation variation due to proximity to piping.
FIG. 2B is an end view of the electrode tip assembly shown in FIG. 2A.

Turning to FIGS. 2A and 2B, electrode tip assembly 300 is an alternate embodiment having an upstanding wall 303 extending radially around a single electrode 200. The upstanding wall 303 has openings 306 to provide for flow through the electrode tip assembly 300. The structure shields the electrode 200 from loss of conduction resulting from the exposure of the electrode 200 to the inside walls of the conduit to which the conductivity sensor 10 is connected.

Figures 3A, 3B:
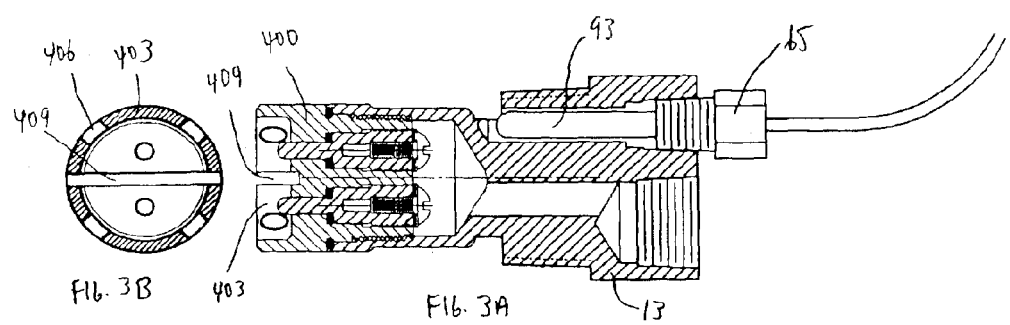
FIG. 3A is a sectional side view of another alternate electrode tip assembly.
FIG. 3B is an end view of the electrode tip assembly shown in FIG. 3A.

In FIGS. 3A and 3B, a second alternate embodiment is shown, electrode tip assembly 400 also includes any upstanding wall 403 having openings 406 defined therein. The upstanding wall 403 includes openings 406 extends radially around the periphery of the electrode tip assembly 400. A groove 409 disposed through the center of the assembly provides for inserting a screw driver or the like for removing the assembly 400 from the probe body 13. The upstanding wall 403 shields the electrodes from loss of conduction.

Figures 4A, 4B:
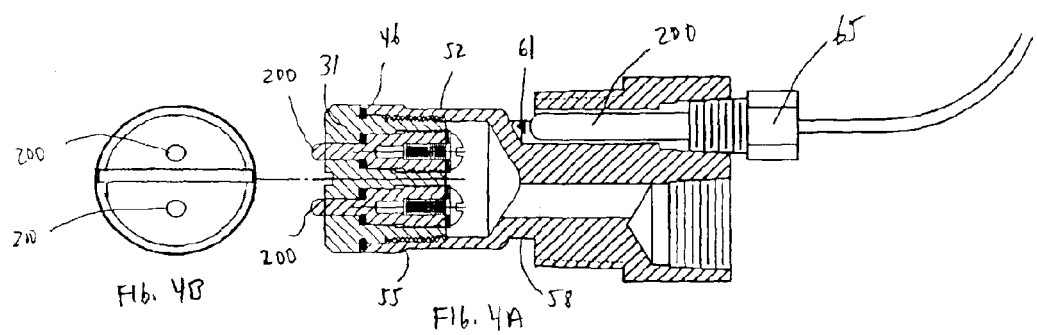
FIG. 4A is a sectional side view of another alternate electrode tip assembly.
FIG. 4B is an end view of the electrode tip assembly shown in FIG. 4A.

In FIGS. 4A and 4B; the electrode tip assembly 31 of FIG. 1 is shown in greater detail.

Figures 5A, 5B:
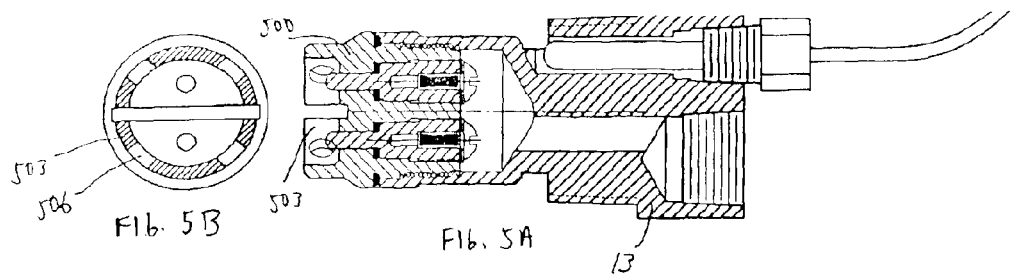
FIG. 5A is a sectional side view of another alternate embodiment of the electrode tip assembly that provides less fluid resistance due to the reduced end diameter; and, FIG. 5B is an end view of the electrode tip assembly shown in FIG. 5A.

In FIGS. 5A and 5B, a third alternate embodiment is shown. Electrode tip assembly 500 also includes an upstanding all 503 having opening 506.

The present invention provides the following advantages. The conductivity probe of the present invention is easily upgradeable from thermistor to RTD technology. Previous units are not interchangeable and therefore the entire unit would have to be discarded to perform an upgrade to new technology. Also, the assembly does not require any potting of electric components which reduces assembly time and reduces the risk of damage to the wiring during assembly. The electrode tip assembly is sealed prior to assembly and only requires connection of wires at its terminals.

Also, there are only three O-rings required and each of the O-rings is a face seal. The terminal block is color coded for ease of assembly and the electrodes are exposed for cleaning.

While the invention has been described in connection with certain embodiments, it is not intended to limit the scope of the invention to the particular forms set forth, but, on the contrary, it is intended to cover such alternatives, modifications, and equivalents as may be included within the spirit and scope of the invention.

What is claimed is:

1. A modular conductivity sensor, comprising:
a probe body having a distal end and a proximal end, the distal end defining a first opening, the first opening being surrounded by a recessed portion forming a shoulder, the probe body having a set of internal threads disposed thereon and having a set of external threads disposed thereon, the probe body having a chamber extending to the first opening; and
an electrode tip assembly having a distal end and a proximal end, the tip assembly including a body formed of an insulating material, the body having a set of threads capable of engaging with the internal threads in the probe body, the tip assembly having a head with a diameter that is greater than the body so as to form a shoulder, the body having at least one opening extending to at least one chamber, the electrode tip assembly having at least one electrode disposed in the at least one chamber in the body, the at least one electrode having a first end extending beyond the distal end of the tip assembly and having a connection terminal disposed at the proximal end of the assembly.

2. A modular conductivity sensor, comprising:
a probe body having a distal end and a proximal end, the distal end defining a first opening, the first opening being surrounded by a recessed portion forming a shoulder, the probe body having a set of internal threads disposed thereon and having a set of external threads disposed thereon, the probe body having a chamber extending to the first opening; and
an electrode tip assembly having a distal end and a proximal end, the tip assembly including a body formed of an insulating material, the body having a set of threads capable of engaging with the internal threads in the probe body, the tip assembly having a head with a diameter that is greater than the body so as to form a shoulder, the body having at least one opening extending to at least one chamber, the electrode tip assembly having at least one electrode disposed in the at least one chamber in the body, the at least one electrode having a first end extending beyond the distal end of the tip assembly and having a connection terminal disposed at the proximal end of the assembly; and a seal disposed on the shoulder of the tip assembly and capable of engaging with the recessed portion on the probe body to provide a seal between the tip assembly and the probe body.

3. A modular conductivity sensor, comprising:
a probe body having a distal end and a proximal end, the distal end defining a first opening, the first opening being surrounded by a recessed portion forming a shoulder, the probe body having a set of internal threads disposed thereon and having a set of external threads disposed thereon, the probe body having a chamber extending to the first opening; and
an electrode tip assembly having a distal end and a proximal end, the tip assembly including a body formed of an insulating material, the body having a set of threads capable of engaging with the internal threads in the probe body, the tip assembly having a head with a diameter that is greater than the body so as to form a shoulder, the body having at least one opening extending to at least one chamber, the electrode tip assembly having at least one electrode disposed in the at least one chamber in the body, the at least one electrode having a first end extending beyond the distal end of the tip assembly and having a connection terminal disposed at the proximal end of the assembly; and,
wherein the at least one chamber in the electrode tip assembly has a shoulder formed therein.

4. The modular conductivity sensor of claim 3, wherein the at least one electrode has a shoulder such that a face seal provides for a seal between the at least one electrode and the electrode tip assembly.

5. A modular conductivity sensor, comprising:
a probe body having a distal end and a proximal end, the distal end defining a first opening, the first opening being surrounded by a recessed portion forming a shoulder, the proximal end having a second and a third opening defined therein, the probe body having a set of internal threads disposed thereon, the probe body having a chamber extending from the first opening to a bottom wall, the bottom wall having a fourth opening defined therein, the probe body having a set of external threads disposed thereon, the fourth opening being connected to the second opening by a first passageway, the third opening being connected to a fifth opening on the body by a second passageway;

an electrode tip assembly having a distal end and a proximal end, the tip assembly including a body formed of an insulating material, the body having a set of threads capable of engaging with the internal threads in the probe body, the tip assembly having a head with a diameter that is greater than the body so as to form a shoulder, the body having at least one opening extending to at least one chamber, the electrode tip assembly having at least one electrode disposed in the at least one chamber in the body, the at least one electrode having a first end extending beyond the distal end of the tip assembly and having a connection terminal disposed at the proximal end of the assembly;

a temperature compensation probe disposed in the third opening in the probe body; and, a wire conduit disposed in the second opening in the probe body.

6. The modular conductivity sensor of claim 5, further comprising a seal disposed on the shoulder of the tip assembly and capable of engaging with the recessed portion on the probe body to provide a seal between the tip assembly and the probe body.

7. The modular conductivity sensor of claim 5, wherein the at least one chamber in the electrode tip assembly has a shoulder formed therein.

8. The modular conductivity sensor of claim 7, wherein the at least one electrode has a shoulder such that a face seal provides for a seal between the at least one electrode and the electrode tip assembly.

9. The modular conductivity sensor of claim 5, wherein the probe body has a reduced diameter section disposed adjacent to the fifth opening.

10. The modular conductivity sensor of claim 5 wherein the temperature compensation probe is thermistor based.

11. The modular conductivity sensor of claim 5, wherein the temperature compensation probe is an RTD.

12. The modular conductivity sensor of claim 5, wherein the probe body has wrench flats formed thereon.

13. The modular conductivity sensor of claim 5, wherein the tip assembly includes an upstanding wall at least partially surrounding the at least one electrode.

14. The modular conductivity sensor of claim 5, wherein the electrode tip assembly has a groove formed in the distal end, the groove capable of receiving a tool.

15. The modular conductivity sensor of claim 5, wherein the fifth opening is disposed between the distal end and the external threads of the probe body.

16. A modular conductivity sensor, comprising:

A modular conductivity sensor, comprising:

a probe body having a distal end and a proximal end, the distal end defining a first opening, the first opening being surrounded by a recessed portion forming a shoulder, the proximal end having a second and a third opening defined therein, the probe body having a set of internal threads disposed thereon, the probe body having a chamber extending from the first opening to a bottom wall, the bottom wall having a fourth opening defined therein, the probe body having a set of external threads disposed thereon, the fourth opening being connected to the second opening by a first passageway, the third opening being connected to a fifth opening on the body by a second passageway;

an electrode tip assembly having a distal end and a proximal end, the tip assembly including a body formed of an insulating material, the body having a set of threads capable of engaging with the internal threads in the probe body, the tip assembly having a head with a diameter that is greater than the body so as to form a shoulder, the body having at least one opening extending to at least one chamber, the electrode tip assembly having at least one electrode disposed in the at least one chamber in the body, the at least one electrode having a first end extending beyond the distal end of the tip assembly and having a connection terminal disposed at the proximal end of the assembly;

a temperature compensation probe disposed in the third opening in the probe body;

a wire conduit disposed in the second opening in the probe body; and, a junction box connected to the wire conduit and having a port for receiving an input from the temperature compensation probe, the junction box including a color-coded terminal block.

17. The modular conductivity sensor of claim 16, further comprising a seal disposed on the shoulder of the tip assembly and capable of engaging with the recessed portion on the probe body to provide a seal between the tip assembly and the probe body.

18. The modular conductivity sensor of claim 16, wherein the at least one chamber in the electrode tip assembly has a shoulder formed therein.

19. The modular conductivity sensor of claim 18, wherein the at least one electrode has a shoulder such that a face seal provides for a seal between the at least one electrode and the electrode tip assembly.

20. The modular conductivity sensor of claim 16, wherein the probe body has a reduced diameter section disposed adjacent to the fifth opening.

21. The modular conductivity sensor of claim 16 wherein the temperature compensation probe is thermistor based.

22. The modular conductivity sensor of claim 16, wherein the temperature compensation probe is an RTD.

23. The modular conductivity sensor of claim 16, wherein the probe body has wrench flats formed thereon.

24. The modular conductivity sensor of claim 16, wherein the tip assembly includes an upstanding wall at least partially surrounding the at least one electrode.

25. The modular conductivity sensor of claim 16, wherein the electrode tip assembly has a groove formed in the distal end, the groove capable of receiving a tool.

26. The modular conductivity sensor of claim 16, wherein the fifth opening is disposed between the distal end and the external threads of the probe body.

27. A method of sensing the conductivity of boiler water, comprising:

providing a probe body having a distal end and a proximal end, the distal end defining a first opening, the first opening being surrounded by a recessed portion forming a shoulder, the proximal end having a second and a third opening defined therein, the probe body having a set of internal threads disposed thereon, the probe body having a chamber extending from the first opening to a bottom wall, the bottom wall having a fourth opening defined therein, the probe body having a set of external threads disposed thereon, the fourth opening being connected to the second opening by a first passageway, the third opening being connected to a fifth opening on the body by a second passageway; an electrode tip assembly having a distal end and a proximal end, the tip assembly including a body formed of an insulating material, the body having a set of threads capable of engaging with the internal threads in the probe body, the tip assembly having a head with a diameter that is greater than the body so as to form a shoulder, the body having at least one opening extending to at least one chamber, the electrode tip assembly having at least one electrode disposed in the at least one chamber in the body, the at least one electrode having a first end extending beyond the distal end of the tip assembly and having a connection terminal disposed at the proximal end of the assembly; a temperature compensation probe disposed in the third opening in the probe body; and, a wire conduit disposed in the second opening in the probe body;

attaching the electrode tip assembly to the probe body to form a conductivity sensor;

installing the conductivity sensor into a port in a boiler via engagement of the external threads with threads disposed in the port; and, monitoring the conductivity of the boiler water to monitor the purity of the water.

* * * * *